United States Patent [19]
Otter et al.

[11] Patent Number: 5,545,629
[45] Date of Patent: Aug. 13, 1996

[54] 5-ETHOXY-2'-DEOXYURIDINES

[75] Inventors: Brian A. Otter, Harrison; Edward L. Schwartz, White Plains, both of N.Y.

[73] Assignee: Montefiore Medical Center, Bronx, N.Y.

[21] Appl. No.: 226,493

[22] Filed: Apr. 12, 1994

[51] Int. Cl.$^6$ ........................................ A61K 31/70
[52] U.S. Cl. ............................ 514/50; 536/28.53
[58] Field of Search ............................ 514/50; 536/28.53

[56] References Cited

FOREIGN PATENT DOCUMENTS 0427587 10/1990 European Pat. Off. .
442757 8/1991 European Pat. Off. .

OTHER PUBLICATIONS

Pharmacology, Chemotherapy 18:269–273, 1973 pp. 269–273, K. K. Gauri et al.
Biochemical Pharmacology, vol. 31, No. 22, pp. 3673–3682, 1982, Great Britain, Jan Balzarini et al.
Journal of Medicinal Chemistry, 1978, vol. 21, No. 2, pp. 228–231, Paul F. Torrence et al.
Antimicrobial Agents and Chemotherapy, 1978, vol. 1 13, No. 2, pp. 545–547, E. De Clercq et al.
Registry File Sheet RN 37805–95–1, 1991.
Stout et al., J. Heterocycl. Chem. 9(3), 545–9.

*Primary Examiner*—Phyllis G. Spivack
*Attorney, Agent, or Firm*—Hedman, Gibson & Costigan, P.C.

[57] ABSTRACT

A composition comprising 5-ethoxy-2'-deoxyuridine is disclosed which is useful as an antiviral agent.

2 Claims, No Drawings

5-ETHOXY-2'-DEOXYURIDINES

BACKGROUND OF THE INVENTION

1. Field of the Invention

This invention relates to the novel chemical compound 5-ethoxy-2'-deoxyuridine which is useful in the treatment of neoplastic diseases.

Other substituted 5-alkoxy-2'-deoxyuridines are described in the prior art which do not have an ethoxy group in the '5' position.

The compound of the invention is of special utility in combination with 5-fluorouracil and α-interferon for the treatment of malignant neoplasms. In addition, the compound 5-ethoxy-2'-deoxyuridine is less toxic than many other prior art 5-substituted-2'-deoxyuridines that have been tested.

Accordingly, it is a primary object of this invention to prepare a novel deoxyuridine compound which is useful as a potentiating agent for anti-neoplastic agents.

It is also an object of the invention to provide a novel pharmaceutical composition which is based on 5-ethoxy-2'-deoxyuridine.

It is also an object of the invention to provide a novel method of treating neoplasms which is based on the administration of an effective amount of 5-ethoxy-2'-deoxyuridine in combination with other anti-neoplastic agents.

These and other objects of the invention will become apparent from a review of the specification.

2. Detailed Description of the Invention

The compound 5-ethoxy-2'-deoxyuridine may be synthesized using the general procedure which is set forth in Otter et al. J. Org. Chem.,36, 1251–1255 (1971) and 37,2858–2863 (1972) and Torrence et al. J. Med. Chem.,21, 228–231 (1977) which are incorporated by reference. This compound may be employed as an anti-viral agent in vitro in a liquid carrier such as water at a level of from 0.2 to 200 mcg./ml and preferably 1 to 20 mcg./ml or in vivo at a dose of 5 to 50 mg./kg and preferably from 3 to 20 mg/kg. of body weight. The viruses which will be susceptible to 5-deoxy-2'-deoxyuridine include vaccina virus, herpes simplex virus type 1 and 2; herpes (varicella) zoster virus; cytomegalovirus; Epstein-Barr virus; hepatitis B virus and the like.

The compound of the invention may also be employed with a combination of the following drugs:

(a) 5-fluorouracil which is given at a dose of 600 to 1000 mg/m$^2$ given daily for 4 to 10 days parenterally, preferably intravenously in divided doses or continuously followed by 4 to 10 days of rest.

(b) interferon-α which is given at a dose of 2 to 40 and preferably 5 to 9 million international units 3 to 7 times per week subcutaneously.

The compound of the invention may be administered orally or parenterally in combination with conventionally employed solvents or solid diluents. It is contemplated that aqueous isotonic solutions will be the preferred compositions with sodium chloride being added in sufficient quantities to make the composition isotonic. Examples of such conventionally employed materials are described in Remington's Pharmaceutical Sciences. 1985 Ed., Mack Publishing Co., Easton, Pa. Chapters 85, 86 and 90, which are incorporated by reference.

DESCRIPTION OF THE PREFERRED EMBODIMENTS

EXAMPLE

The compound 5-ethoxy-2'-deoxyuridine was synthesized from 5-hydroxy-2'-deoxyuridine according to the following procedure:

The compound 5-hydroxy-2'-deoxyuridine was prepared by modifying the procedure described in the literature (E. G. Podrebarac and C. C. Cheng, Synthetic Procedures in Nucleic Acid Chemistry, Vol. 1, p412–413, W. W. Zorbach and R. S. Tipson Eds., Interscience Publishers, NY 1968) as follows: bromine (1.1 ml, 1 equivalent) is added dropwise at room temperature to a stirred solution of 5 g. of 2'-deoxyuridine (Sigma) in 100 ml of water until a pale color persisted. The color was then discharged by the addition of a small crystal of sodium thiosulfate. Pyridine (25 ml) was added in one portion and the mixture was held at room temperature for 17 hours. Solvents were then removed by evaporation in vacuo and ethanol (3×50ml) was added to and evaporated from the syrupy residue. A solution of the final residue in 50 ml of ethanol deposited colorless crystals of 2'-deoxy-5-hydroxyuridine when held for 5 hours at 5° C. The yield of the first crop was 2.3 g.

The 2'-deoxy-5-hydroxyuridine (244 mg.,1 mmol) was suspended in a mixture of methanol (10 ml) and water (5 ml) at room temperature, and 1 ml of 1.0N sodium hydroxide solution (1 mmol) was added to generate the monoanion. Ethyl bromide (0.312 ml, 4 mmol) was added, and the reaction mixture was stirred for 16 hours. The solvent was removed in vacuo, and ethanol was added to and evaporated from the residue. The desired 5-ethoxy product was separated from small amounts of the 3-ethyl-5-ethoxy dialkyl byproduct by chromatography on a silica gel column using chloroform-methanol (9:1, v/v) as the solvent. Following crystallization from absolute ethanol, 5-ethoxy-2'-deoxyuridine was obtained in 52% yield (140mg); mp 179°–181° C.; $^1$H NMR (methyl sulfoxide-d$_6$),δ6 11.38 (1H, br s, NH), 7.58 (1H, s, H-6), 6.18 (1H, t, H-1'), 5.19 (1H, d, 3'-OH), 5.09 (1H, t, 5'-OH), 4.25 (1H, m, H-3'), 3.79 (3H, m. H4' and OCH$_2$CH$_3$), 3.59 (2H, br s,H-5' and H-5"), 2.10 (2H, m, H-2' and H-2") and 1.23 ppm (3H, t, OCH$_2$CH$_3$).

Anal. Calcd. for C$_{11}$H$_{16}$N$_2$O$_6$ C, 48.53; H, 5.92; N, 10.29. Found: C, 48.69; H, 6.0-1; N, 10.36.

For assessment of the antitumor activity of 5-ethoxy-2'-deoxyuridine, an in vitro clonogenic assay was used. The assay was based on a modification of procedures first described by Puck and Marcus (Proc. Natl. Acad. Sci. (USA) 41:432–437, 1955). Clonogenic assays using human tumor cells measure effects on the reproductive potential of drug treated tumor cells and approximate more closely than other in vitro assays the desired target of chemotherapy (P. Roper and B. Drewinko, Cancer Res. 39:1428–1430, 1979) In particular, clonogenic assays of fluoropyrimidines using human colan carcinoma cell lines have been shown to reasonably closely predict factors which affect tumor responsiveness clinically (B. Drewinko et al. Cancer 45:1144–1158,1980; B. Drewinko and L. Y. Yang, Cancer Treat. Rep. 69:1391–1398, 1985; R. G. Moran and K. L. Scanlon, Cancer Res. 51:4618–4623, 1991; J. A. Houghton et al. Cancer Commun. 3:225–231, 1991; A. F. Sobrero et al., J. Natl. Cancer Inst. 85:1937–1944, 1993).

HT-29 human carcinoma cells (ATCC No. HTB-38) were maintained in RPMI 1640 with 10% v/v fetal bovine serum (GIBCO) in a humidified, 5% $CO_2$ atmosphere at 37° C. Cells were plated in 24 well plates (150 cells per well) in RPMI 1640 medium with 10% v/v dialyzed fetal bovine serum. After allowing cell attachment to proceed overnight, combinations of interferon-α (500 units/ml; Roferon-A, Roche Labs.), 5-ethoxy-2'-deoxyuridine (150 μM), in the presence of increasing concentrations of 5-fluorouracil (as specified in the Table) were added. The various agents were diluted in phosphate-buffered saline, and control wells received vehicle alone. After 72 hours, drug containing medium was removed and replaced with RPMI 1640 with 10% v/v fetal bovine serum. Cell colonies were allowed to grow for an additional 7–10 days, at which point they were stained and counted. Control cloning efficiency in the absence of drug averaged 60%; all data are expressed relative to the control cloning efficiency. Data are means of at least 3 determinations. The $IC_{50}$ values for 5-fluorouracil were calculated graphically by determining the concentration of 5-fluorouracil that reduced cloning efficiency by 50% from the cloning efficiency value measured in the absence of 5-fluorouracil.

| | Cloning Efficiency (% of control) | | | |
|---|---|---|---|---|
| 5-FU | CONT | IFN | 5-ETH | 5-ETH +IFN |
| 0 | 100%b | 95% | 89% | 97% |
| 0.025 μM | — | — | — | 89% |
| 0.05 μM | — | — | 81% | 81% |
| 0.10 μM | — | — | 80% | 38% |
| 0.15 μM | — | — | — | 9% |
| 0.25 μM | 104% | 97% | 60% | 0% |
| 0.50 μM | 93% | 83% | 38% | — |
| 1.0 μM | 87% | 56% | 13% | — |
| 1.5 μM | 60% | 18% | 4% | — |
| 2.0 μM | 55% | 8% | — | — |
| 3.0 μM | 27% | 1% | — | — |
| 4.0 μM | 5% | — | — | — |
| | Cloning Efficiency (% of control) | | | |
| 5-FU | CONT | IFN | 5-ETH | 5-ETH +IFN |
| $IC_{50}$ | 2.0 μM | 1.1 μM | 0.35 μM | 0.08 μM |

5FU = 5-fluorouracil
Cont = control, PBS (vehicle)
IFN = interferon-α (Roferon-A, Roche Labs) 500u/ml
5-ETH = 5-ethoxy-21-deoxyuridine (150 μM)

The growth inhibitory effect of 5-ethoxy-2'-deoxyuridine was compared with other analogous 5-substituted-2'-deoxyuridine compounds by determining the $IC_{50}$ of each compound in an assay which measured the growth inhibition of HT-29 cells. The HT-29 cells were placed in 96 well plates ($2\times10^4$ cells per well) in RPMI 1640 with 10% added fetal bovine serum. After allowing the cells to attach overnight, several concentrations of the test compounds were added. After 6 days, cell numbers were quantitated by staining with sulforhodamine B (Skehan et al., J. Natl. Canc. Inst, 82, 1107–1112, 1990). The results were as follows:

| Compound | $IC_{50}$ |
|---|---|
| 5-methoxy-21-deoxyuridine | 28 μM |
| 5-ethoxy-21-deoxyuridine | 750 μM |
| 5-propyloxy-2'-deoxyuridine | 325 μM |
| 5-ethyl-2'-deoxyuridine | 2.5 μM |
| 5-propynyloxy-2'-deoxyuridine | >3000 μM |

This test data establishes that the compound of the invention, 5-ethoxy-2'-deoxyuridine, has about 1/27 of the toxicity of the methyloxy analog, about 1/2 of the toxicity of the propyloxy analog and about 1/300 of the toxicity of the ethyl analog. This difference in cytotoxicity is unexpected.

We claim:

1. A pharmaceutical composition which comprises 5-ethoxy-2'-deoxyuridine and a pharmaceutical carrier.

2. A method of inhibiting a virus, said method comprising contacting a virus with a virus inhibiting effective amount of 5-ethoxy-2'-deoxyuridine.

* * * * *